United States Patent
Hirai et al.

(10) Patent No.: US 7,462,300 B2
(45) Date of Patent: *Dec. 9, 2008

(54) DOPED-TYPE METAL SULFIDE PHOSPHOR NANOPARTICLE, DISPERSION THEREOF, AND METHOD FOR PRODUCING THE SAME

(75) Inventors: Hiroyuki Hirai, Minami-ashigara (JP); Keiko Sugihara, Minami-ashigara (JP); Junji Nishigaki, Minami-ashigara (JP)

(73) Assignee: FujiFilm Corporation, Minato-Ku, Tokyo (JP)

( * ) Notice: Subject to any disclaimer, the term of this patent is extended or adjusted under 35 U.S.C. 154(b) by 204 days.

This patent is subject to a terminal disclaimer.

(21) Appl. No.: 10/982,876

(22) Filed: Nov. 8, 2004

(65) Prior Publication Data

US 2005/0121648 A1    Jun. 9, 2005

(30) Foreign Application Priority Data

Nov. 10, 2003 (JP) ............... 2003-380437
Feb. 26, 2004 (JP) ............... 2004-052021

(51) Int. Cl.
*C09K 11/56* (2006.01)
*B82B 1/00* (2006.01)
*C01G 9/08* (2006.01)

(52) U.S. Cl. .............. 252/301.6 S; 977/834; 977/824

(58) Field of Classification Search ........... 252/301.6 S, 252/301.4 S; 977/834, 824
See application file for complete search history.

(56) References Cited

U.S. PATENT DOCUMENTS

| 5,985,173 | A | * | 11/1999 | Gray et al. ............. 252/301.4 R |
| 6,106,609 | A | * | 8/2000 | Yang et al. .................... 117/11 |
| 6,319,426 | B1 | | 11/2001 | Bawendi et al. |
| 6,558,575 | B2 | * | 5/2003 | Andriessen et al. ... 252/301.6 S |
| 2003/0030067 | A1 | * | 2/2003 | Chen ......................... 257/102 |

FOREIGN PATENT DOCUMENTS

JP    2002-38145    *    2/2002

OTHER PUBLICATIONS

M. Ihara et al., "Cathodoluminescence and Photoluminescence of Nanocrystal Phosphors", Journal of The Electrochemical Society, vol. 149, No. 3, 2002, pp. H72-H75.

* cited by examiner

*Primary Examiner*—C. Melissa Koslow
(74) *Attorney, Agent, or Firm*—Buchanan Ingersoll & Rooney PC

(57) ABSTRACT

A doped-type metal sulfide phosphor nanoparticle, whose surface is modified with a surface modifier, the surface modifier being a compound of formula [I]:

$$\text{HS-L-W} \qquad \text{Formula [I]}$$

wherein L is a divalent linking group; and W is COOM or $NH_2$, in which M is a hydrogen atom, an alkali metal atom, or $NX_4$, in which X is a hydrogen atom or an alkyl group; a dispersion containing the nanoparticle; and a method of producing the nanoparticle or the dispersion.

5 Claims, No Drawings

DOPED-TYPE METAL SULFIDE PHOSPHOR NANOPARTICLE, DISPERSION THEREOF, AND METHOD FOR PRODUCING THE SAME

FIELD OF THE INVENTION

The present invention relates to a doped-type metal sulfide phosphor nanoparticle which is applicable, for example, to a fluorescently-labeling material and a luminescent device; a dispersion thereof; and a method for producing the nanoparticle or of the dispersion.

BACKGROUND OF THE INVENTION

It is known that a nanometer-size particulate material can exhibit properties distinct from those of the corresponding bulk material. For example, a semiconductor is well known for the so-called quantum size effect, in which the band gap, which had been believed to be material-specific, varies with particle size. The particle size at which this effect is significant is generally from a few nm to tens of nm, depending on the type of semiconductor material. Thus, a singlenano-particle is particularly important. Some materials are also known for another effect, in which, as the quantum size effect becomes significant, the fluorescence lifetime becomes short, and a certain luminescence becomes to be observed, which would otherwise not be observed. As mentioned above, nano-sized materials, in particular single-nanosized materials, can exhibit properties different from the known properties of the corresponding bulk materials, and thus are attracting widespread attention in science and engineering.

A certain semiconductor nanoparticle phosphor material is proposed that comprises a semiconductor nanoparticle, for example, of CdSe/CdS (core/shell), CdSe/ZnS (core/shell), or the like, and the semiconductor nanoparticle is utilized to form beads whose surface is coupled to a molecule probe for detecting a target molecule (see, for example, Science, Vol. 281, No. 25, 1998, pp. 2013-2016, and Nature Biotechnology, Vol. 19, 2001, pp. 631-6354). These semiconductor nanoparticles of different crystallite sizes can produce different wavelengths of emission. If the labeled beads are encoded with respect to a combination of luminescence wavelength and luminescence intensity, simultaneous multiple measurements are possible. The semiconductor nanoparticle phosphor material has good properties for a labeling material, such as high sensitivity, low cost, and easiness of automation. Using the semiconductor nanoparticle phosphor material as a labeling material, therefore, a specific site of a living organism, a certain substance in plasma, or the like, can be detected at high sensitivity and high speed.

Another semiconductor nanoparticle phosphor material is proposed that comprises a semiconductor nanoparticle whose surface is coated with a modifying molecule, so as to have improved affinity to the matrix (for example, see U.S. Pat. No. 6,319,426, JP-A-2002-38145 ("JP-A" means unexamined published Japanese patent application), JP-A-2003-64278; and Science, Vol. 281, No. 25, 1998, pp. 2016-2018). The semiconductor nanoparticle coated with the modifying molecule can have improved affinity to an aqueous medium, and/or improved dispersibility in an organic macromolecule or an organic solvent. Thus, the semiconductor nanoparticle phosphor material can easily be applied as a labeling material, and a luminescent material can easily be produced by dispersing the semiconductor nanoparticle phosphor material into a resin. The semiconductor nanoparticle phosphor material is therefore expected to be widely applied in the fields of optical devices, clinical diagnosis, biochemical research or medical science research, or the like.

However, the use of the semiconductor nanoparticle phosphor material of CdSe or CdSe/ZnS (core/shell) or the like may raise safety issues and environmental issues. Therefore, alternatives are desired that are safe and have less influence on the environment. A useful alternative is a nanoparticle phosphor material of zinc sulfide (ZnS) doped with manganese ion ($Mn^{2+}$) or the like, which material can easily be synthesized in a solvent, such as water. Compared with the case of the above semiconductor nanoparticle phosphor material, it is difficult to control the luminescence wavelength of the zinc sulfide (ZnS) nanoparticle phosphor material by varying its crystallite size. On the other hand, the ZnS nanoparticle phosphor material is advantageous in that its luminescence wavelength can be varied with the type of the doping metal ion or the surface-modifying molecule (surface modifier) (for example, see JP-A-2002-322468; Journal of the Illuminating Engineering Institute of Japan, Vol. 87, No. 4, 2003, pp. 256-261; and Journal of The Electrochemical Society, Vol. 149, No. 3, 2002, pp. H72-H75).

However, the zinc sulfide (ZnS)-based nanoparticle phosphor material has a relatively large surface area, such that it can significantly cause secondary aggregation, thus the zinc sulfide (ZnS)-based nanoparticle phosphor material cannot easily form a transparent colloidal dispersion, and it can hardly be functionalized for the purpose of application to fluorescent labeling materials or luminescent devices. JP-A-2002-38145 discloses ZnS-based nanoparticles having a specific amino group-containing compound fixed on the surface by condensation reaction. However, it has been found that such a compound does not always have sufficient dispersibility in a specific solvent, such as water.

SUMMARY OF THE INVENTION

The present invention resides in a doped-type metal sulfide phosphor nanoparticle, whose surface is modified with a surface modifier, the surface modifier being a compound represented by formula [I]:

$$HS-L-W \qquad \text{Formula [I]}$$

wherein L represents a divalent linking group; and W represents COOM or $NH_2$, in which M represents a hydrogen atom, an alkali metal atom, or $NX_4$, in which X represents a hydrogen atom or an alkyl group.

Further, the present invention resides in a doped-type metal sulfide phosphor nanoparticle dispersion, wherein the doped-type metal sulfide phosphor nanoparticle is dispersed in water and/or a hydrophilic solvent.

Further, the present invention resides in a doped-type metal sulfide phosphor nanoparticle dispersion, wherein the doped-type metal sulfide phosphor nanoparticle is dispersed in a hydrophobic organic solvent.

Further, the present invention resides in a method of producing a doped-type metal sulfide phosphor nanoparticle whose surface is modified with a surface modifier, which comprises the steps of:

carrying out a reaction of a doping metal ion and a matrix metal ion, with a sulfide ion, in water and/or a hydrophilic solvent by a coprecipitation method; and adding thereto a surface modifier comprising the compound represented by formula [I].

Further, the present invention resides in a method of producing a dispersion of a doped-type metal sulfide phosphor nanoparticle whose surface is modified with a surface modifier, which comprises the steps of:

carrying out a reaction of a doping metal ion and a matrix metal ion, with a sulfide ion, in water and/or a hydrophilic solvent by a coprecipitation method; and adding thereto a surface modifier comprising the compound represented by formula [I].

Further, the present invention resides in a method of producing a dispersion of a doped-type metal sulfide phosphor nanoparticle, which comprises the steps of:

carrying out a reaction of a doping metal ion and a matrix metal ion, with a sulfide ion, in the presence of a nitrogen-containing heterocyclic compound in water and/or a hydrophilic solvent; and adding thereto the compound represented by formula [I].

Further, the present invention resides in a method of producing a dispersion of a doped-type metal sulfide phosphor nanoparticle, which comprises the steps of:

carrying out a reaction of a doping metal ion and a matrix metal ion, with a sulfide ion, by a reverse micelle method in a non-water soluble organic solvent containing a trace amount of water;

adding thereto the compound represented by formula [I]; and adding a good solvent for the compound represented by formula [I], to perform re-dispersion.

Further, the present invention resides in a fluorescent-labeling material, wherein an affinity molecule is coupled to the doped-type metal sulfide phosphor nanoparticle.

Further, the present invention resides in a method of producing a fluorescent-labeling material, which comprises the step of:

coupling an affinity molecule, to a terminal group of the surface modifier which covers the doped-type metal sulfide phosphor nanoparticle.

Other and further features and advantages of the invention will appear more fully from the following description.

DETAILED DESCRIPTION OF THE INVENTION

According to the present invention, there are provided the following means:

(1) A doped-type metal sulfide phosphor nanoparticle, whose surface is modified with a surface modifier, the surface modifier being a compound represented by formula [I]:

HS-L-W            Formula [I]

wherein L represents a divalent linking group; and W represents COOM or $NH_2$, in which M represents a hydrogen atom, an alkali metal atom, or $NX_4$, in which X represents a hydrogen atom or an alkyl group;

(2) The doped-type metal sulfide phosphor nanoparticle according to the above item (1), wherein the metal sulfide is zinc sulfide;

(3) A doped-type metal sulfide phosphor nanoparticle dispersion, wherein the doped-type metal sulfide phosphor nanoparticle according to the above item (1) or (2) is dispersed in water and/or a hydrophilic solvent;

(4) The doped-type metal sulfide phosphor nanoparticle dispersion according to the above item (3), containing a nitrogen-containing heterocyclic compound in the dispersion;

(5) A doped-type metal sulfide phosphor nanoparticle dispersion, wherein the doped-type metal sulfide phosphor nanoparticle according to the above item (1) or (2) is dispersed in a hydrophobic organic solvent;

(6) A method of producing a doped-type metal sulfide phosphor nanoparticle whose surface is modified with a surface modifier, comprising the steps of:

carrying out a reaction of a doping metal ion and a matrix metal ion, with a sulfide ion, in water and/or a hydrophilic solvent by a coprecipitation method; and adding thereto a surface modifier comprising a compound represented by formula [I]:

HS-L-W            Formula [I]

wherein L represents a divalent linking group; and W represents COOM or $NH_2$, in which M represents a hydrogen atom, an alkali metal atom, or $NX_4$, in which X represents a hydrogen atom or an alkyl group;

(7) The method of producing a doped-type metal sulfide phosphor nanoparticle according to the above item (6), wherein the reaction is carried out under conditions that the total number of moles of the doping metal ion and the matrix metal ion is greater than the number of moles of the sulfide ion;

(8) The method of producing a doped-type metal sulfide phosphor nanoparticle according to the above item (6) or (7), comprising the step of: performing purification by centrifugal separation, after adding the compound represented by formula [I];

(9) The method of producing a doped-type metal sulfide phosphor nanoparticle according to the above item (6) or (7), comprising the step of: performing purification by ultrafiltration, after adding the compound represented by formula [I];

(10) The method of producing a doped-type metal sulfide phosphor nanoparticle according to any one of the above items (6) to (9), comprising the step of: performing freeze-drying or vacuum-drying;

(11) A method of producing a dispersion of a doped-type metal sulfide phosphor nanoparticle whose surface is modified with a surface modifier, comprising the steps of:

carrying out a reaction of a doping metal ion and a matrix metal ion, with a sulfide ion, in water and/or a hydrophilic solvent by a coprecipitation method; and adding thereto a surface modifier comprising a compound represented by formula [I]:

HS-L-W            Formula [I]

wherein L represents a divalent linking group; and W represents COOM or $NH_2$, in which M represents a hydrogen atom, an alkali metal atom, or $NX_4$, in which X represents a hydrogen atom or an alkyl group;

(12) A method of producing a dispersion of a doped-type metal sulfide phosphor nanoparticle, comprising the steps of:

carrying out a reaction of a doping metal ion and a matrix metal ion, with a sulfide ion, in the presence of a nitrogen-containing heterocyclic compound in water and/or a hydrophilic solvent; and adding thereto a compound represented by formula [I]:

HS-L-W            Formula [I]

wherein L represents a divalent linking group; and W represents COOM or $NH_2$, in which M represents a hydrogen atom, an alkali metal atom, or $NX_4$, in which X represents a hydrogen atom or an alkyl group;

(13) A method of producing a dispersion of a doped-type metal sulfide phosphor nanoparticle, comprising the steps of:

carrying out a reaction of a doping metal ion and a matrix metal ion, with a sulfide ion, by a reverse micelle method in a non-water soluble organic solvent containing a trace amount of water;
    adding thereto a compound represented by formula [I]; and
    adding a good solvent for the compound represented by formula [I], to perform re-dispersion:

HS-L-W     Formula [I]

wherein L represents a divalent linking group; and W represents COOM or $NH_2$, in which M represents a hydrogen atom, an alkali metal atom, or $NX_4$, in which X represents a hydrogen atom or an alkyl group;

(14) The method of producing a dispersion of a doped-type metal sulfide phosphor nanoparticle according to any one of the above items (11) to (13), wherein the reaction is carried out under conditions that the total number of moles of the doping metal ion and the matrix metal ion is greater than the number of moles of the sulfide ion;

(15) The method of producing a dispersion of a doped-type metal sulfide phosphor nanoparticle according to any one of the above items (11) to (14), comprising the step of: performing purification by centrifugal separation;

(16) The method of producing a dispersion of a doped-type metal sulfide phosphor nanoparticle according to any one of the above items (11) to (14), comprising the step of: performing purification by ultrafiltration;

(17) A fluorescent-labeling material, wherein an affinity molecule is coupled to the doped-type metal sulfide phosphor nanoparticle according to the above item (1) or (2); and

(18) A method of producing a fluorescent-labeling material, comprising the step of:
    coupling an affinity molecule, to a terminal group of the surface modifier which covers the doped-type metal sulfide phosphor nanoparticle according to the above item (1) or (2).

The present invention is described in detail below.

As a result of active investigations in view of the above problems in the conventional techniques, the inventors of the present invention have found that, when the compound represented by formula [I] is used as a surface modifier, well-dispersible metal sulfide nanoparticle materials can be obtained, and that zinc sulfide-based nanoparticle phosphor materials can be obtained that have high sensitivity and uniform luminescent properties and can easily be functionalized. The present invention has been attained based on these findings.

[1] Surface Modifier

According to the present invention, the dispersibility of a collection of metal sulfide nanoparticles in a solvent can be improved, using the surface modifier of the compound represented by formula [I] (hereinafter also referred to as the surface modifier for use in the present invention). Using the surface modifier also produces the advantage that a molecule probe for detecting a target molecule can easily be coupled thereto.

HS-L-W     Formula [I]

In the formula, L represents a divalent linking group, and W represents COOM or $NH_2$, wherein M represents a hydrogen atom, an alkali metal atom, or $NX_4$, wherein X represents a hydrogen atom or an alkyl group.

Examples of the linking group include an alkylene group (e.g. a chain-like or cyclic alkylene group having generally 1 to 20 carbon atoms, preferably 1 to 18 carbon atoms, such as methylene, ethylene, trimethylene, tetramethylene, hexamethylene, propylene, ethylethylene, and cyclohexylene).

The linking group may have an unsaturated bond. Examples of such an unsaturated group include an alkenylene group (e.g. a chain-like or cyclic alkenylene group having generally 1 to 20 carbon atoms, preferably 1 to 18 carbon atoms, such as vinylene, propenylene, 1-butenylene, 2-butenylene, 2-pentenylene, 8-hexadecenylene, 1,3-butanedienylene, and cyclohexenylene), an alkynylene group (e.g. an alkynylene group having generally 1 to 20 carbon atoms, preferably 1 to 18 carbon atoms, such as ethynylene and propynylene), and an arylene group (e.g. an arylene group having generally 6 to 14 carbon atoms, such as phenylene, naphthylene and anthrylene, preferably a phenylene group of 6 carbon atoms).

The linking group may have at least one hetero atom (the hetero atom means any atom other than a carbon atom, e.g. a nitrogen atom, an oxygen atom and a sulfur atom). The hetero atom is preferably an oxygen atom or a sulfur atom, most preferably an oxygen atom. The number of hetero atoms is preferably, but not particularly limited to, at most five, more preferably at most three.

A partial structure of the linking group may have a functional group which contains a carbon atom adjacent to the hetero atom. Examples of such a functional group include an ester group (including a carboxylate group, a carbonate group, a sulfonate group, and a sulfinate group), an amido group (including a carboxylic acid amide group, a urethane group, a sulfonic acid amide group, and a sulfinic acid amide group), an ether group, a thioether group, a disulfide group, an amino group, and an imido group. Any of the above functional groups may also have a substituent, and L may have a plurality of any of the above functional groups. Such plural groups may be the same or different from each other.

The functional group is preferably an ester group, an amido group, an ether group, a thioether group, a disulfide group, or an amino group, more preferably an alkenyl group, an ester group, or an ether group.

In the case where W is $NH_2$, W may form a salt with hydrochloric acid, sulfuric acid, nitric acid, phosphoric acid, sulfonic acid, or the like. The alkali metal atom represented by M may be lithium (Li), sodium (Na), potassium (K), or the like. The alkyl group represented by X may be a chain-like alkyl group having generally 1 to 20 carbon atoms, preferably 1 to 18 carbon atoms, such as methyl, ethyl, n-propyl, isopropyl, tert-butyl, octyl, and cetyl. The four X groups may be independently any of the above, and they may be the same or different from each other.

Specific examples of the surface modifier for use in the present invention include mercaptoacetic acid, 2-mercaptopropionic acid, 3-mercaptopropionic acid, 2-mercaptobutyric acid, 4-mercaptobutyric acid, 8-mercaptooctanoic acid, 1-mercaptoundecanoic acid, 18-mercaptostearic acid, 3-mercaptoacrylic acid, mercaptomethacrylic acid, 4-mercaptocrotonic acid, 18-mercaptooleic acid, thiomalic acid, mercaptopropiolic acid, 4-mercaptophenylhydrocinnamic acid, 2-mercaptoethylamine, 2-mercaptopropylamine, 3-mercaptopropylamine, 3-mercapto-n-butylamine, 4-mercapto-n-butylamine, 2-mercapto-tert-butylamine, 8-mercaptooctylamine, 11-mercaptoundecylamine, 18-mercaptostearylamine, 18-mercaptooleylamine, 5-aminopentanoic acid (2-mercapto-ethyl)-amide, 6-aminohexanoic acid (2-mercapto-ethyl)-amide, 11-aminoundecanoic acid (2-mercapto-ethyl)-amide, 5-aminopentanoic acid-3-mercapto-propyl ester, 11-aminoundecanoic acid-3-mercaptopropyl ester, 3-(11-aminoundecyloxy)-propane-1-thiol, (2-mercapto-ethylamino)-acetic acid-2-[2-(2-aminoacetoxy)-ethoxy]-ethyl ester. The above amino group-containing compound may form a salt with an acid as stated above. These examples are not intended to limit the scope of the present invention.

In the case where water is used as the dispersion solvent, the number of carbons of L in the surface modifier for use in the present invention is preferably from 1 to 5, more preferably from 1 to 4. In the case where an organic solvent is used as the dispersion solvent, the number of carbons of L is preferably from 6 to 20, more preferably from 6 to 18. Another surface modifier (e.g. polyethylene glycol, polyoxyethylene (1) lauryl ether phosphate, lauryl ether phosphate, trioctylphosphine, trioctylphosphine oxide, sodium polyphosphate, sodium bis(2-ethylhexyl)sulfosuccinate, and the like) may coexist during or after the synthesis of the nanoparticles.

[2] Doped-type Metal Sulfide Phosphor Nanoparticles

Examples of the metal to constitute the doped-type metal sulfide phosphor nanoparticle of the present invention include a Group II metal, e.g. zinc (Zn), cadmium (Cd), and strontium (Sr); preferably zinc (Zn) which is less toxic and can form a relatively stable sulfide in water or a hydrophilic solvent. Examples of the doping activator include metals, e.g. manganese (Mn), copper (Cu), europium (Eu), terbium (Tb), thulium (Tm), aluminum (Al), and silver (Ag), and a compound of any of the above metals in combination with chlorine (Cl) or fluorine (F). The doping activator does not have to consist of a single type of atom, and it may comprise different kinds of atoms. The luminescence wavelength may vary with the activator. For example, manganese (Mn)-doped zinc sulfide (ZnS) (hereinafter represented by "ZnS:Mn") can show an orange luminescence, and europium (Eu)-doped zinc sulfide can show a red luminescence. The optimal concentration of the activator is preferably from 0.001 to 10 atomic percent, depending on the type of the activator.

The number average particle diameter of the metal sulfide phosphor nanoparticle is preferably from 0.5 to 100 nm, more preferably from 0.5 to 50 nm, still more preferably from 1 to 10 nm. The particle size distribution of the phosphor nanoparticles is preferably from 0 to 50%, more preferably from 0 to 20%, still more preferably from 0 to 10%, in terms of coefficient of variation. Herein, the coefficient of variation means a percentage value obtained through dividing the arithmetic standard deviation by the number average particle diameter (arithmetic standard deviation×100/number average particle diameter).

[3] Methods of Producing a Metal Sulfide Phosphor Nanoparticle and a Dispersion Thereof (1) Coprecipitation Method The doped-type metal sulfide phosphor nanoparticles may be obtained by a process including the steps of: dissolving a salt for the doping metal ion and a salt for the matrix metal ion in water and/or a hydrophilic solvent (e.g. methanol, ethanol, acetonitrile, and tetrahydrofuran), to form a solution; dissolving a sulfide such as sodium sulfide and ammonium sulfide in water and/or a hydrophilic solvent, to form another solution; and mixing both solutions while stirring them at a high speed by a single-jet method or a double-jet method. The reaction temperature is generally from 0 to 100° C., preferably from 3 to 80° C.; and the reaction time is generally from one second to 60 minutes, preferably one minute to 30 minutes. In this process, the synthesis of the metal sulfide phosphor nanoparticles is preferably performed in the presence of a nitrogen-containing heterocyclic compound so that a colloidal dispersion having good dispersibility can be obtained. Preferred examples of the nitrogen-containing heterocyclic compound include imidazoles (such as benzimidazole, 2-hydroxybenzimidazole, and 7-hydroxy-5-methylbenzimidazole), indoles (such as 4-hydroxyindole and 5-hydroxy-3-methylindole), pyrazoles (such as indazole and 5-methyl-1,2-benzopyrazole), and triazoles (such as benzotriazole, 1H-benzotriazole-1-methanol, 1H-1,2,3-triazolo[4,5-b]pyridine, 3H-1,2,3-triazolo[4,5-b]pyridine-3-ol, 7-hydroxy-5-methyl-1,3,4-triazaindolizine, and 7-hydroxy-1,2,4-triazolo[4,3-a]pyridine). The addition amount of the nitrogen-containing heterocyclic compound is generally from 0.05 to 100 molar times, preferably from 0.1 to 20 molar times the amount of the metal sulfide.

After this process, a dispersion of the metal sulfide phosphor nanoparticles may be produced, by adding the surface modifier for use in the present invention to the reaction product (the surface modifier may be previously dissolved in water and/or a hydrophilic solvent before added). The addition amount of the surface modifier for use in the present invention is generally from 0.05 to 100 molar times, preferably from 0.1 to 20 molar times the amount of the metal sulfide. The amount of the surface modifier coupled to the surface of the particles may vary with the size and concentration of the particles, the type of the surface modifier (such as size and structure), and the like, but it is generally from about 0.005 to about 10 molar times, preferably from about 0.01 to about 2 molar times the amount of the metal sulfide.

It is not preferred that the doped-type metal sulfide phosphor nanoparticles are synthesized in the presence of the surface modifier for use in the present invention, because the luminescence intensity may significantly be reduced. Therefore, the surface modifier for use in the present invention is added after the synthesis of the metal sulfide phosphor nanoparticles.

The doped-type metal sulfide phosphor nanoparticles may be washed and purified by centrifugation, filtration or the like, and then the resultant particles may be dispersed into a solvent containing the surface modifier for use in the present invention.

The thus-prepared doped-type metal sulfide phosphor nanoparticle dispersion, which contains the surface modifier for use in the present invention, may be subjected to repeated centrifugation or decantation with water and/or a hydrophilic solvent, so that metal sulfide phosphor nanoparticles free from salt byproducts and the excessive amount of the surface modifier for use in the present invention can be obtained. Alternatively, the doped-type metal sulfide phosphor nanoparticle dispersion, containing the surface modifier for use in the present invention, prepared according to the above method, may be centrifuged or filtrated, and the resulting supernatant or filtrate may be subject to ultrafiltration, so that a colloidal dispersion of metal sulfide phosphor nanoparticles free from salt byproducts and the excessive amount of the surface modifier for use in the present invention can be obtained. When the metal sulfide phosphor nanoparticles are produced in the form of a fine powder, the above dispersion or a dispersion synthesized by a reverse micelle method as described later is preferably subjected to freeze drying or vacuum drying at a low temperature of, for example, 50° C. or lower. In particular, the fine powder produced by freeze-drying is preferred because it can easily be dispersed again in a solvent.

The concentration of the nanoparticles in the dispersion of the doped-type metal sulfide phosphor nanoparticles of the present invention is preferably from 0.05 mM to 1,000 mM, more preferably from 0.1 mM to 500 mM.

In the above coprecipitation method, the concentration of the metal sulfide in the reaction liquid for producing nanoparticles may be set in a relatively wide range from 0.1 mM to 1,000 mM, but is preferably set in the range from 0.5 mM to 500 mM. The metal sulfide phosphor nanoparticles are preferably synthesized under the conditions that the total number of moles of the doping metal ion and the matrix metal ion is greater by at least 1%, preferably 2 to 40%, than the number of moles of the sulfide ion. In this case, there is provided an advantage that the zeta potential of the resulting metal sulfide can be positive so that the surface modifier for use in the present invention can be easily adsorbed on it.

(2) Reverse Micelle Method

To a reverse micelle solution (I) of a mixture of an aqueous solution of a metal salt (e.g. zinc acetate and manganese acetate) and a non-water soluble organic solvent (hereinafter also referred to as "hydrophobic organic solvent") containing a surfactant, is added another reverse micelle solution (II) of a mixture of an aqueous solution of a sulfide (a sulfide, for example, of an alkali metal or ammonia) and a non-water soluble organic solvent containing a surfactant, to form doped-type metal sulfide phosphor nanoparticles. The reaction temperature is generally from 0 to 90° C., preferably from 3 to 60° C., and the reaction time is generally from one minute to 60 minutes, preferably from three minutes to 30 minutes. In each of the reverse micelle solutions (I) and (II), the mass ratio of water to the surfactant (water/surfactant) is generally 20 or less, preferably from 0.1 to 10. In the reaction liquid for forming nanoparticles, the concentration of the metal sulfide is generally from 0.1 mM to 100 mM, preferably from 0.5 mM to 50 mM. In this method, the metal sulfide phosphor nanoparticles are also preferably synthesized under the conditions that the total number of moles of the doping metal ion and the matrix metal ion is greater by at least 1%, preferably 2 to 40%, than the number of moles of the sulfide ion.

After the doped-type metal sulfide phosphor nanoparticles are formed, a certain process is preferably performed which includes the steps of: adding the surface modifier for use in the present invention (if necessary, the surface modifier may be added in the form of a water and/or primary alcohol solution); precipitating the phosphor nanoparticles; and adding a good solvent for the surface modifier for use in the present invention to the resultant precipitate, to re-disperse the precipitate, for the purpose of washing and dispersing the precipitate.

As the surfactant, an oil-soluble surfactant may be used. Specific examples of the oil-soluble surfactant include sulfonate types (e.g., sodium bis(2-ethylhexyl)sulfosuccinate), quaternary ammonium salt types (e.g., cetyltrimethylammonium bromide), and ether types (e.g., pentaethylene glycol dodecyl ether).

Preferable examples of the water-insoluble organic solvent for use in dissolving the surfactant include alkanes and ethers. The alkanes are preferably those having 7 to 12 carbon atoms. Specifically, heptane, octane, nonane, decane, iso-octane, undecane, and dodecane are preferable. The ethers are preferably diethyl ether, dipropyl ether, and dibutyl ether. The amount of the surfactant in the water-insoluble organic solvent is preferably 20 to 200 g/L. Further, in the reverse micelle solution (I) and the reverse micelle solution (II), the surfactant to be used may be the same or different form each other, and the mass ratio range of water to the surfactant may be the same as or different.

Because the phosphor nanoparticle formation reaction infers great influence on the monodispersibility of the distribution of particle diameter, it is preferable to run the reaction with stirring at a rate as high as possible. A preferable stirring apparatus is a stirrer having high shearing force. In detail, the apparatus is such a stirrer having a structure, in which the stirring blade basically has a turbine-type or paddle-type structure, also a sharp edge is attached to a position where it is in contact with the end of the blade or with the blade, and the blade is rotated using a motor. Specifically, as the stirrer, Dissolver (manufactured by Tokushu Kika Kogyo Co., Ltd.), Omni Mixer (manufactured by Yamato Scientific Co., Ltd.), and Homogenizer (manufactured by SMT) are useful. The use of each of these apparatuses makes it possible to synthesize a monodispersed nanoparticle in the form of a stable dispersion.

[4] Fluorescent Label Material

The nano phosphor particles having the coating of the surface modifier represented by formula [1] may also be coupled to a specific affinity molecule, such as nucleic acids (e.g. nucleic acid monomers, oligonucleotides, and the like), antibodies (e.g. monoclonal antibodies, any other proteins and amino acids), and polysaccharides, via a terminal reactive group of the surface modifier, such as an amino group and a carboxyl group, by, for example, an amidation reaction for forming a peptide bond. The product coupled to the affinity molecule may be allowed to bind to a specific biomolecule, to serve as a fluorescent label material. When such a fluorescent label material is used, the biomolecule or the like may be a native material (e.g. in vivo) or a foreign material (e.g. in vitro).

The amidation reaction may be a condensation reaction of a carboxyl group or any derivative group thereof (such as an ester group, an acid anhydride group, and an acid halide group) with an amino group. The acid anhydride or the acid halide is preferably used together with a base. In the reaction using a methyl or ethyl ester of the carboxylic acid, heating or reducing pressure is preferably performed for the purpose of removing an alcohol produced. In the case where direct amidation of the carboxyl group is carried out, an amidation reaction-accelerating substance/agent, which includes an amidation reagent such as DCC, Morpho-CDI and WSC, a condensation additive such as HBT, and an active ester agent such as N-hydroxyphthalimide, p-nitrophenyl trifluoroacetate, and 2,4,5-trichlorophenyl, may be allowed to coexist or react in advance. In the amidation process, any one of the carboxyl group and the amino group of the affinity molecule to be coupled by amidation is preferably protected with a suitable blocking group according to a usual method, and then deprotected after the reaction.

The nanoparticle phosphor coupled to the affinity molecule by the amidation reaction, may be washed and purified in a usual manner such as gel filtration, and then dispersed in water and/or a hydrophilic solvent (preferably methanol, ethanol, isopropanol, or 2-ethoxyethanol) before use. In such a dispersion, the nanoparticle phosphor may have any concentration that can vary depending on fluorescent intensity and is not particularly limited, but it preferably has a concentration of $10^{-1}$ M to $10^{-15}$ M, more preferably a concentration of $10^{-2}$ M to $10^{-10}$ M.

The presence of the coating of the modifier molecule on the surface of the phosphor nanoparticles may be confirmed, by identifying a constant distance between the particles in the observation with high-resolution TEM such as FE-TEM, and by chemical analysis.

According to the present invention, a doped-type metal sulfide phosphor nanoparticle having good dispersibility, a dispersion thereof, and methods for producing them, can be provided. In particular, according to the present invention, a doped-type metal sulfide phosphor nanoparticle that has high sensitivity, uniform luminescent properties, safety, and less influence on the environment, and that can easily be functionalized; a dispersion thereof, and methods for producing them, can be provided. Further, according to the present invention, a fluorescent-labeling material that allows high-sensitivity, high-speed detection of a specific site of a living organism, a certain substance in plasma, or the like, in a simple system or apparatus, can be provided.

The doped-type metal sulfide phosphor nanoparticle of the present invention can form a stable water-based colloidal dispersion or a stable hydrophobic organic solvent-based colloidal dispersion. The dispersion of the surface modifier-covered, doped-type metal sulfide phosphor nanoparticle according to the present invention, may be allowed to react with a protein such as an antibody (to form, for example, a peptide bond), such that it can function as a marker (a fluorescent-labeling material) for a specific substance in a living organism, or the like.

The present invention will be described in more detail based on examples given below, but the invention is not meant to be limited by these.

EXAMPLES

Example 1

In 60 ml of water, were dissolved 15 g of zinc acetate 2 hydrate and 0.5 g of manganese acetate 4 hydrate, to prepare a solution, which is designated as Solution 1. In 60 ml of water, was dissolved 12.4 g of sodium sulfide 9 hydrate, to prepare a solution, which is designated as Solution 2. The resultant Solutions 1 and 2 were simultaneously added to 80 ml of water in a 300-ml beaker at a speed of 10 ml/minute, while the water was vigorously stirred. Thus, a white precipitate was produced, and it showed a strong orange fluorescence when irradiated with 302 nm ultraviolet light. To the product, was added 20 g of 2-mercaptopropylamine hydrochloride, followed by stirring for 30 minutes. The resultant mixture was then allowed to stand, and the resultant supernatant was filtrated with a 0.2-μm filter. The filtrate showed a strong orange fluorescence when irradiated with 302 nm ultraviolet light. The filtrate was ultrafiltrated using a filter with a molecular-weight cutoff of 10,000. Water was further added thereto, and washing and ultrafiltration were repeated, to remove the salts and the excessive amount of the 2-mercaptopropylamine and to purify the resultant colloidal dispersion of ZnS:Mn. The colloidal dispersion was filtrated with a 0.2-μm filter, and the filtrate (designated as Sample 1) was measured for fluorescence spectrum at an excitation wavelength of 306 nm. As a result, an orange luminescence having a maximum at about 590 nm was observed. The concentration of the nanoparticles in the filtrate was 16 mM. The average crystallite size of the produced ZnS:Mn was determined to be 2.8 nm, by XRD measurement. The particle size distribution of the phosphor nanoparticles was 15% in terms of coefficient of variation.

Example 2

Samples 2 to 5 were prepared in the same manner as Sample 1 in Example 1, except that, although the molar ratio between the zinc acetate 2 hydrate and the manganese acetate 4 hydrate was the same as Sample 1, the total number of moles of the acetates was changed relative to the number of moles of the sodium sulfide, as shown in Table 1 below. The fluorescence spectrum of each sample was measured. The relative intensity of the luminescence is shown in Table 1.

Example 3

Samples 6 to 11 were prepared in the same manner as Sample 1 in Example 1, except that a different kind of surface modifier was used, as shown in Table 1. The fluorescence spectrum of each sample was measured. The relative intensity of the luminescence is shown in Table 1.

TABLE 1

| Sample No. | Surface modifier | Molar ratio*[1] | Relative luminescence intensity*[2] |
|---|---|---|---|
| 1 | 2-Mercaptopropylamine hydrochloride | 1.11 | +++ |
| 2 | 2-Mercaptopropylamine hydrochloride | 1.20 | +++ |
| 3 | 2-Mercaptopropylamine hydrochloride | 1.05 | +++ |
| 4 | 2-Mercaptopropylamine hydrochloride | 1.00 | ++ |
| 5 | 2-Mercaptopropylamine hydrochloride | 0.90 | + |
| 6 | 2-Mercaptoethylamine hydrochloride | 1.11 | +++ |
| 7 | 3-Mercapto-n-butylamine hydrochloride | 1.11 | ++ |
| 8 | 2-Mercapto-t-butylamine ½ sulfate | 1.11 | +++ |
| 9 | 3-Mercaptopropylamine hydrochloride | 1.11 | +++ |
| 10 | 2-Mercaptonicotinic acid | 1.11 | ± |
| 11 | Butylamine hydrochloride | 1.11 | ± |

*[1]The ratio of the total number of moles of the Zn and Mn salts to the number of moles of sodium sulfide
*[2]+++ Very high intensity, ++ high intensity, + medium intensity, ± almost no fluorescence was observed In Table 1, Samples 1 to 9 (Examples according to the present invention) each showed excellent results, contrary to those of Samples 10 and 11 (Comparative Examples). It has been found that the luminescence intensity of each of Samples 1 to 3 and 6 to 9, in which the total number of moles of the metal salts (the zinc salt and the manganese salt) was larger than the number of moles of sodium sulfide, was higher than that of Sample 4 or 5 (Examples which did not satisfy the requirements as stated in the above item (14)). It has also been found that the surface modifier for use in the present invention can produce quite high luminescence intensity.

Comparative Example 1

Comparative Example to the Invention According to the Above Item (11)

A sample was prepared in the same manner as in Example 1, except that 2-mercaptoethylamine had been added to the water in advance, to which the Solutions 1 and 2 were added simultaneously. As a result, the luminescence intensity was significantly reduced (luminescence intensity: ±). It has been found that the surface modifier for use in the present invention is preferably added after the formation of the nanoparticle phosphor of ZnS:Mn.

Example 4

In 60 ml of water, was dissolved 6.46 g of zinc chloride, to prepare a solution, which is designated as Solution 3. Separately, in 80 ml of water, was dissolved 42 mg of copper chloride, to prepare a solution, which is designated as Solution 4. Further, in 60 ml of water, was dissolved 10.4 g of sodium sulfide 9 hydrate, to prepare a solution, which is designated as Solution 5. To Solution 4 vigorously stirred, was added 50 μl of Solution 5. Solution 3 and the remainder of Solution 5 were simultaneously added thereto, at a rate of 10 ml/minute. After the addition was completed, the mixture was further stirred for 10 minutes. Then, 200 ml of a 10-mass % aqueous solution of 2-mercaptopropylamine hydrochloride, which is a surface modifier for use in the present invention, was added thereto, followed by stirring for 10 minutes and then allowing to stand for 10 days. The resulting supernatant was filtrated with a 0.2-μm filter, and the filtrate was measured for fluorescence spectrum at an excitation wavelength of 312 nm. As a result, a blue-green luminescence (luminescence intensity: ++) having a maximum at about 490 nm was observed. The particle size distribution of the phosphor nanoparticles was 21% in terms of coefficient of variation.

Comparative Example 2

Comparative Example to the Invention According to the Above Item (14)

A sample was prepared in the same manner as in Example 4, except that the amount of the sodium sulfide 9 hydrate to be used was increased to 12.7 g, and that the number of moles of sodium sulfide was changed such that it would be greater by 10% than the number of moles of the metal salts. As a result, the luminescence intensity was reduced (luminescence intensity: +). It has been found that the total number of moles of the metal salts is also preferably greater than the number of moles of sodium sulfide, in the case of the nanoparticle phosphor of ZnS:Cu.

Example 5

To 150 ml of n-heptane, were added 21.3 g of sodium bis(2-ethylhexyl)sulfosuccinate (AOT) and 5.2 g of water. They were mixed and stirred at 3,000 rpm for 10 minutes with a homogenizer, to prepare a micelle solution, which is designated as Micelle solution I. Was weighed 133 mg of sodium sulfide 9 hydrate, and this was then added to and mixed with 20 ml of the Micelle solution I, to prepare a solution, which is designated as Solution A.

Were weighed 101 mg of zinc acetate and 13 mg of manganese acetate 4 hydrate, and they were then added to and mixed with 80 ml of the Micelle solution I, to prepare a solution, which is designated as Solution B.

Using a homogenizer, Solution B was stirred at 3,000 rpm for 10 minutes, and Solution A was added thereto, followed by stirring for 10 minutes, to form a mixture, in which the total number of moles of the metal salts was 1.1 times the number of moles of sodium sulfide. Thus, a clear dispersion of ZnS:Mn colloid was formed. To the dispersion, was added 300 ml of a 5%-methanol solution of 3-mercaptopropylamine nitrate, followed by gentle stirring and then allowing to stand. The resulting supernatant was removed by decantation, and 300 ml of methanol was added to the residue, followed by gentle stirring and then allowing to stand. The supernatant was removed by decantation, and 50 ml of water was added to the precipitate. Thus, an aqueous colloidal dispersion of ZnS:Mn whose surface was modified with 3-mercaptopropylamine, was obtained.

The dispersion was measured for fluorescence spectrum at an excitation wavelength of 325 nm. As a result, an orange luminescence having a maximum at about 590 nm was observed (luminescence intensity: +++). The concentration of the nanoparticles in the filtrate was 7 mM. The average crystallite size of the thus-produced ZnS:Mn was determined to be 4.2 nm, by XRD measurement. The particle size distribution of the phosphor nanoparticles was 14% in terms of coefficient of variation.

Comparative Example 3

Comparative Example to the Invention According to the Above Item (14)

An aqueous colloidal dispersion of ZnS:Mn surface-modified with 3-mercaptopropylamine, was prepared in the same manner as in Example 5, except that the amounts of the zinc acetate and the manganese acetate 4 hydrate to be used in Solution B were changed to 87 mg and 11 mg, respectively, and that the total number of moles of the metal salts was changed to be 0.94 times the number of moles of sodium sulfide. As a result, the fluorescence intensity was reduced (luminescence intensity: +). It has been found that the total number of moles of the metal salts is preferably greater than the number of moles of sodium sulfide also in the case where a reverse micelle method is used for the synthesis of ZnS:Mn phosphor nanoparticles.

Example 6

A sample was prepared in the same manner as in Example 5, except that a 5%-methanol solution of 18-mercaptooleylamine was used in washing in place of the solution of 3-mercaptopropylamine, and then 50 ml of toluene was added thereto. Thus, a toluene colloidal dispersion of ZnS:Mn whose surface was modified with 18-mercaptooleylamine, was obtained. The luminescence performance of this dispersion was the same as that of the aqueous colloidal dispersion in Example 5.

It has been found that the doped-type metal sulfide phosphor nanoparticles synthesized according to the reverse micelle method, can be made to be dispersible in a hydrophobic organic solvent, as well as a water-based solvent, by using the surface modifier for use in the present invention properly selected among those having different carbon atoms (namely having different solubility parameters).

Example 7

In 600 ml of water, were dissolved 11 g of zinc acetate 2 hydrate and 0.37 g of manganese acetate 4 hydrate, to prepare a solution, which is designated as Solution 1. To 15 g of 7-hydroxy-5-methyl-1,3,4-triazaindolizine, was added 680 ml of water, followed by heating at 80° C. to dissolve the compound in the water and further adding 120 ml of Solution 1 thereto, to prepare a solution, which is designated as Solution 2. Separately, in 600 ml of water, was dissolved 12.4 g of sodium sulfide 9 hydrate, to prepare a solution, which is designated as Solution 3. While Solution 2 was kept at 80° C. and vigorously stirred, the remainder of Solution 1 and the above Solution 3 were simultaneously added thereto, at a rate of 8 ml/minute and at a rate of 10 ml/minute, respectively. Thus, a translucent colloidal dispersion was obtained. To 50 ml of the colloidal dispersion, was added 6.5 ml of a 0.1-M solution of 2-mercaptopropylamine hydrochloride, followed by mixing them. The resulting colloidal dispersion showed a strong orange fluorescence (luminescence intensity: +++) having a maximum at about 590 nm when irradiated with 330-nm ultraviolet light. XRD measurement revealed that ZnS:Mn nanoparticles were produced with an average crystallite size of 3 nm.

Example 8

To the colloidal dispersion of the ZnS:Mn nanoparticle phosphor prepared in Example 7, was added NaHCO$_3$ such that the concentration would be 0.1% by mass, and the pH was adjusted to 7.5. Thereto, was added a 1-mass % aqueous solution of sulfosuccinimidyl:D-biotin (manufactured by DOJINDO LABORATORIES) as a biotin labeling agent, to carry out an amidation reaction. The reaction product was purified by gel filtration, to give a $10^{-3}$-M aqueous dispersion of ZnS:Mn nanoparticle phosphor to which biotin was coupled as a functional molecule. Using this dispersion, avidin was fluorescently labeled, to detect.

Example 9

In 60 ml of water, were dissolved 15 g of zinc acetate 2 hydrate and 0.5 g of manganese acetate 4 hydrate, to prepare a solution, which is designated as Solution 1. In 60 ml of water, was dissolved 12.4 g of sodium sulfide 9 hydrate, to prepare a solution, which is designated as Solution 2. The resultant Solutions 1 and 2 were simultaneously added to 80 ml of water in a 300-ml beaker at a speed of 10 ml/minute, while the water was vigorously stirred. Thus, a white precipitate was produced, and it showed a strong orange fluorescence when irradiated with 302 nm ultraviolet light. To the product, was added 40 ml of 2-mercaptopropionic acid, followed by stirring for 30 minutes. The resultant mixture was then allowed to stand, and the resultant supernatant was filtrated with a 0.2-μm filter. The filtrate showed a strong orange fluorescence when irradiated with 302 nm ultraviolet light. The filtrate was ultrafiltrated using a filter with a molecular-weight cutoff of 10,000. Water was further added thereto, and washing and ultrafiltration were repeated, to remove the salts and the excessive amount of the 2-mercaptopropionic acid and to purify the resultant colloidal dispersion of ZnS:Mn. The colloidal dispersion was filtrated with a 0.2-μm filter, and the filtrate (designated as Sample 1a) was measured for fluorescence spectrum at an excitation wavelength of 306 nm. As a result, an orange luminescence having a maximum at about 590 nm was observed. The concentration of the nanoparticles in the filtrate was 20 mM. The average crystallite size of the produced ZnS:Mn was determined to be 2.8 nm, by XRD measurement. The particle size distribution of the phosphor nanoparticles was 15% in terms of coefficient of variation.

Example 10

Samples 2a to 5a were prepared in the same manner as Sample 1a in Example 9, except that, although the molar ratio between the zinc acetate 2 hydrate and the manganese acetate 4 hydrate was the same as Sample 1a, the total number of moles of the acetates was changed relative to the number of moles of the sodium sulfide, as shown in Table 2 below. The fluorescence spectrum of each sample was measured. The relative intensity of the luminescence is shown in Table 2.

Example 11

Samples 6a to 12a were prepared in the same manner as Sample 1a in Example 9, except that a different kind of surface modifier was used, as shown in Table 2. The fluorescence spectrum of each sample was measured. The relative intensity of the luminescence is shown in Table 2.

TABLE 2

| Sample No. | Surface modifier | Molar ratio*[1] | Relative luminescence intensity*[2] |
|---|---|---|---|
| 1a | 2-Mercaptopropionic acid | 1.11 | +++ |
| 2a | 2-Mercaptopropionic acid | 1.20 | +++ |
| 3a | 2-Mercaptopropionic acid | 1.05 | +++ |
| 4a | 2-Mercaptopropionic acid | 1.00 | ++ |
| 5a | 2-Mercaptopropionic acid | 0.90 | + |
| 6a | Mercaptoacetic acid | 1.11 | ++ |
| 7a | Thiomalic acid | 1.11 | +++ |
| 8a | Mercaptomethacryric acid | 1.11 | +++ |
| 9a | Sodium 2-mercaptopropionate | 1.11 | +++ |
| 10a | Sodium thiomalate | 1.11 | +++ |
| 11a | Succinic acid | 1.11 | ± |
| 12a | 2-Mercaptonicotinic acid | 1.11 | ± |

*[1]The ratio of the total number of moles of the Zn and Mn salts to the number of moles of sodium sulfide
*[2]+++ Very high intensity, ++ high intensity, + medium intensity, ± almost no fluorescence was observed In Table 2, Samples 1a to 10a (Examples according to the present invention) each showed excellent results, contrary to those of Samples 11a and 12a (Comparative Examples). It has been found that the luminescence intensity of each of Samples 1a to 3a and 6a to 10a, in which the total number of moles of the metal salts (the zinc salt and the manganese salt) was larger than the number of moles of sodium sulfide, was higher than that of Sample 4a or 5a (Examples which did not satisfy the requirements as stated in the above item (14)). It has also been found that the surface modifier for use in the present invention can produce quite high luminescence intensity.

Comparative Example 4

Comparative Example to the Invention According to the Above Item (11)

A sample was prepared in the same manner as in Example 9, except that mercaptoacetic acid had been added to the water in advance, to which the Solutions 1 and 2 were added simultaneously. As a result, the luminescence intensity was significantly reduced (luminescence intensity: ±). It has been found that the surface modifier for use in the present invention is preferably added after the formation of the nanoparticle phosphor of ZnS:Mn.

Example 12

In 60 ml of water, was dissolved 6.46 g of zinc chloride, to prepare a solution, which is designated as Solution 3. Separately, in 80 ml of water, was dissolved 42 mg of copper chloride, to prepare a solution, which is designated as Solution 4. Further, in 60 ml of water, was dissolved 10.4 g of sodium sulfide 9 hydrate, to prepare a solution, which is designated as Solution 5. To Solution 4 vigorously stirred, was added 50 μl of Solution 5. Solution 3 and the remainder of Solution 5 were simultaneously added thereto, at a rate of 10 ml/minute. After the addition was completed, the mixture was further stirred for 10 minutes. Then, 200 ml of a 20-mass % aqueous solution of thiomalic acid, which is a surface modifier for use in the present invention, was added thereto, followed by stirring for 10 minutes and then allowing to stand for 10 days. The resulting supernatant was filtrated with a 0.2-μm filter, and the filtrate was measured for fluorescence spectrum at an excitation wavelength of 312 nm. As a result, a blue-green luminescence (luminescence intensity: ++) having a maximum at about 490 nm was observed. The particle size distribution of the phosphor nanoparticles was 23% in terms of coefficient of variation.

Comparative Example 5

Comparative Example to the Invention According to the Above Item (14)

A sample was prepared in the same manner as in Example 12, except that the amount of the sodium sulfide 9 hydrate to be used was increased to 12.7 g, and that the number of moles of sodium sulfide was changed such that it would be greater by 10% than the number of moles of the metal salts. As a result, the luminescence intensity was reduced (luminescence intensity: +). It has been found that the total number of moles of the metal salts is also preferably greater than the number of moles of sodium sulfide, in the case of the nanoparticle phosphor of ZnS:Cu.

Example 13

To 150 ml of n-heptane, were added 21.3 g of sodium bis(2-ethylhexyl)sulfosuccinate (AOT) and 5.2 g of water. They were mixed and stirred at 3,000 rpm for 10 minutes with a homogenizer, to prepare a micelle solution, which is designated as Micelle solution I. Was weighed 133 mg of sodium sulfide 9 hydrate, and this was then added to and mixed with 20 ml of the Micelle solution I, to prepare a solution, which is designated as Solution A.

Were weighed 101 mg of zinc acetate and 13 mg of manganese acetate 4 hydrate, and they were then added to and mixed with 80 ml of the Micelle solution I, to prepare a solution, which is designated as Solution B.

Using a homogenizer, Solution B was stirred at 3,000 rpm for 10 minutes, and Solution A was added thereto, followed by stirring for 10 minutes, to form a mixture, in which the total number of moles of the metal salts was 1.1 times the number of moles of sodium sulfide. Thus, a clear dispersion of ZnS:Mn colloid was formed. To the dispersion, was added 300 ml of a 5%-methanol solution of thiomalic acid, followed by gentle stirring and then allowing to stand. The resulting supernatant was removed by decantation, and 300 ml of a 5%-methanol solution of thiomalic acid was, again, added to the residue, followed by gentle stirring and then allowing to stand. The supernatant was removed by decantation, and 50 ml of water was added to the precipitate. Thus, an aqueous colloidal dispersion of ZnS:Mn whose surface was modified with thiomalic acid, was obtained.

The dispersion was measured for fluorescence spectrum at an excitation wavelength of 325 nm. As a result, an orange luminescence having a maximum at about 590 nm was observed (luminescence intensity: +++). The concentration of the nanoparticles in the filtrate was 10 mM. The average crystallite size of the thus-produced ZnS:Mn was determined to be 4.5 nm, by XRD measurement. The particle size distribution of the phosphor nanoparticles was 12% in terms of coefficient of variation.

Comparative Example 6

Comparative Example to the Invention According to the Above Item (14)

An aqueous colloidal dispersion of ZnS:Mn surface-modified with thiomalic acid, was prepared in the same manner as in Example 13, except that the amounts of the zinc acetate and the manganese acetate 4 hydrate to be used in Solution B were changed to 87 mg and 11 mg, respectively, and that the total number of moles of the metal salts was changed to be 0.94 times the number of moles of sodium sulfide. As a result, the fluorescence intensity was reduced (luminescence intensity: +). It has been found that the total number of moles of the metal salts is preferably greater than the number of moles of sodium sulfide also in the case where a reverse micelle method is used for the synthesis of ZnS:Mn phosphor nanoparticles.

Comparative Example 7

A sample was prepared in the same manner as in Example 13, except that a 5% methanol solution of succinic acid was used in washing in place of thiomalic acid, and then 50 ml of water was added thereto. The resulting aqueous dispersion of ZnS:Mn colloid was unstable and suffered sedimentation immediately. It has been found that the doped-type metal sulfide phosphor nanoparticle produced with the surface modifier for use in the present invention, is excellent in stability as a dispersion.

Example 14

A sample was prepared in the same manner as in Example 13, except that a 5%-methanol solution of 11-mercaptoundecanoic acid was used in washing in place of the solution of thiomalic acid, and then 50 ml of toluene was added thereto. Thus, a toluene colloidal dispersion of ZnS:Mn whose surface was modified with 11-mercaptoundecanoic acid, was obtained. The luminescence performance of this dispersion was the same as that of the aqueous colloidal dispersion in Example 13.

It has been found that the doped-type metal sulfide phosphor nanoparticles synthesized according to the reverse micelle method, can be made to be dispersible in a hydrophobic organic solvent, as well as a water-based solvent, by using the surface modifier for use in the present invention properly selected among those having different carbon atoms (namely having different solubility parameters).

Having described our invention as related to the present embodiments, it is our intention that the invention not be limited by any of the details of the description, unless otherwise specified, but rather be construed broadly within its spirit and scope as set out in the accompanying claims.

What we claim is:

1. A method of producing a doped-type zinc sulfide phosphor nanoparticle whose surface is modified with a surface modifier, comprising the steps of:

carrying out a reaction of a doping metal ion and a matrix zinc ion, with a sulfide ion, in water and/or a hydrophilic solvent by a coprecipitation method, in which a solution comprising the doping metal ion and the matrix zinc ion and a solution comprising the sulfide ion are mixed under high speed stirring by a single-jet method or a double-jet method, wherein the total number of moles of the doping metal ion and the matrix zinc ion is greater than the number of moles of the sulfide ion by 2 to 40%; and adding thereto a surface modifier comprising a compound represented by formula [I]:

HS-L-W                                       Formula [I]

wherein L represents a divalent linking group; and W represents COOM or $NH_2$, in which M represents a hydrogen atom, an alkali metal atom, or $NX_4$, in which X represents a hydrogen atom or an alkyl group, wherein the number average particle diameter of the zinc sulfide phosphor nanoparticle is from 1 to 10 nm and the particle size distribution of the zinc sulfide phosphor nanoparticle is from 0 to 20% in terms of coefficient of variation.

2. The method of producing a doped-type zinc sulfide phosphor nanoparticle according to claim 1, comprising the step of: performing purification by centrifugal separation, after adding the compound represented by formula [I].

3. The method of producing a doped-type zinc sulfide phosphor nanoparticle according to claim 1, comprising the step of: performing purification by ultrafiltration, after adding the compound represented by formula [I].

4. The method of producing a doped-type zinc sulfide phosphor nanoparticle according to claim 1, comprising the step of: performing freeze-drying or vacuum-drying.

5. The method of producing a doped-type zinc sulfide phosphor nanoparticle according to claim 1, wherein the doped-type zinc sulfide phosphor nanoparticle is synthesized in the presence of a nitrogen-containing heterocyclic compound.

* * * * *